US005766439A

United States Patent [19]
Eyal et al.

[11] Patent Number: 5,766,439
[45] Date of Patent: Jun. 16, 1998

[54] PRODUCTION AND RECOVERY OF ORGANIC ACIDS

[75] Inventors: Aharon M. Eyal, Jerusalem, Israel; William F. Lehnhardt, Lovington, Ill.

[73] Assignee: A. E. Staley Manufacturing Co., Decatur, Ill.

[21] Appl. No.: 752,803

[22] Filed: Nov. 20, 1996

Related U.S. Application Data

[63] Continuation of Ser. No. 728,836, Oct. 10, 1996, abandoned.

[51] Int. Cl.$^6$ .................... C12P 7/52; C25B 3/00; C07C 51/42; C07C 59/08
[52] U.S. Cl. .................... 204/524; 204/519; 204/522; 204/527; 204/530; 204/534; 204/537; 204/637; 210/259; 210/651; 210/654; 435/135; 435/136; 435/139; 435/142; 435/145; 435/146; 435/803; 562/578; 562/580; 562/586; 562/593
[58] Field of Search .................... 435/135, 136, 435/139, 142, 145, 146, 803; 562/578, 580, 584, 593; 204/519, 522, 524, 527, 530, 534, 537, 637; 210/259, 651, 654

[56] References Cited

U.S. PATENT DOCUMENTS

| | | |
|---|---|---|
| 686,170 | 11/1901 | Waite . |
| 2,223,797 | 12/1940 | Tindall . |
| 2,327,191 | 8/1943 | Kane et al. ............... 195/36 |
| 2,464,487 | 3/1949 | Chappell et al. . |
| 2,710,880 | 6/1955 | Filachione et al. . |
| 3,030,276 | 4/1962 | Thomsen .................. 195/36 |
| 3,810,337 | 5/1974 | Pollard . |
| 3,810,937 | 5/1974 | Kuceski . |
| 3,944,606 | 3/1976 | Rieger et al. . |
| 4,275,234 | 6/1981 | Baniel et al. . |
| 4,334,095 | 6/1982 | Baniel . |
| 4,444,881 | 4/1984 | Urbas . |
| 4,698,303 | 10/1987 | Bailey et al. . |
| 4,771,001 | 9/1988 | Bailey et al. . |
| 4,877,731 | 10/1989 | Ling et al. . |
| 4,963,486 | 10/1990 | Hang . |
| 5,034,105 | 7/1991 | Berglund et al. . |
| 5,068,418 | 11/1991 | Kulprathipanja et al. . |
| 5,071,754 | 12/1991 | Walkup et al. . |
| 5,079,164 | 1/1992 | Kirkovits et al. . |
| 5,089,664 | 2/1992 | Dalcanale et al. . |
| 5,104,492 | 4/1992 | King et al. . |
| 5,143,834 | 9/1992 | Glassner et al. . |
| 5,198,086 | 3/1993 | Chlanda et al. . |
| 5,210,294 | 5/1993 | Mantovani et al. . |
| 5,210,296 | 5/1993 | Cockrem et al. . |
| 5,250,159 | 10/1993 | Butterworth . |
| 5,268,079 | 12/1993 | Ochoa Gomez et al. . |
| 5,352,825 | 10/1994 | Felman et al. . |
| 5,426,219 | 6/1995 | Lehnhardt et al. . |
| 5,453,365 | 9/1995 | Sterzel et al. . |

FOREIGN PATENT DOCUMENTS

| | | |
|---|---|---|
| 0 375 463 | 12/1989 | European Pat. Off. . |
| 0 393 818 | 2/1990 | European Pat. Off. . |
| 0 517 242 A2 | 6/1992 | European Pat. Off. . |
| 2292040 | 6/1976 | France . |
| 146411 | 10/1921 | United Kingdom . |
| 694795 | 7/1953 | United Kingdom . |
| 1004218 | 9/1965 | United Kingdom . |
| WO 93/00440 | 1/1993 | WIPO . |
| WO 93/06226 | 4/1993 | WIPO . |

OTHER PUBLICATIONS

Dietz et al, "Physical Properties of Sodium, Potassium, and Ammonium Lactate Solutions," Industurial and Engineering Chemistry, 33:11, pp. 1444–1447 (Nov. 1941).
Pan et al, "Purification of Lactic Acid From Fermentation of Corn Products," Chemical Abstracts 113:96160c (1990).
Czytko et al, "Continous Gluscose Fermentation for Lactic Acid Production Recovery of Acid by Electrodialysis," Chemical Abstracts 112:117239g (1990).
Eveleva et al, "Lactic Acid," Chemical Abstracts 111:132518v (1989).
Obara, "Purification of Lactic Acid from Fermentation Broth," Chemical Abstracts 111:76553p (1989).
Obara, "Purification of Organic Acid from Fermentation Fluid and Apparatus Therefor," Chemical Abstracts 111:22197g (1989).
Ono et al, "Separation of Lactic Acid by Extraction with Isopropyl Acetate," Chemical Abstracts 110:172707s (1989).
Ono, "Purification of Lactic Acid with Activated Carbon," Chemical Abstracts 110:74833k (1989).
Maenato et al, "Separation and Purification of Lactic Acid," Chemical Abstracts 107:115250b (1987).
Daicel Chemical Industries, Ltd., "Purification of Lactic Acid," Chemical Abstracts 95:203332u (1981).
Griffith et al,"Continuous Lactic Acid Production Using a Fixed–Film System," Chemical Abstracts 92:58182b (1980).
Napierala et al, "Production of Alimentary Lactic Acid of High Purity," Chemical Abstracts 78:135586b (1973).
Vogt et al, "Continuous Recovery of Pure Lactic Acid," Chemical Abstracts 75:117972h (1971).
Chaintron, "Purification of Lactic Acid," Chemical Abstracts 74:41925b (1971).

(List continued on next page.)

*Primary Examiner*—Herbert J. Lilling
*Attorney, Agent, or Firm*—Arnold, White & Durkee

[57] ABSTRACT

A process is described for producing organic acids such as lactic acid. The process includes the steps of producing lactic acid by fermentation, resulting in an aqueous fermentation broth containing lactic acid, and adding a calcium base, such as calcium carbonate, to the fermentation broth, thereby producing calcium lactate in the broth. Biomass is removed from the broth, thereby leaving an aqueous solution or dispersion of calcium lactate. The calcium lactate is reacted with a source of ammonium ions, such as ammonium carbonate, or a mixture of ammonia and carbon dioxide, thereby producing an ammonium lactate. Contaminating cations can be removed by ion exchange. The free lactic acid or a derivative thereof can be separated from the ammonium ions, preferably by salt-splitting electrodialysis.

58 Claims, 5 Drawing Sheets

OTHER PUBLICATIONS

Boroda et al, "Purification and Concentration of Lactic Acid," Chemical Abstracts 70:67528s (1969).

Colin et al, "Extraction of Organic Acids," Chemical Abstracts 69:43459y (1968).

Robatel Inc. proposal (Mar. 3, 1993).

Robatel brochure entitled, "Batteries De Melanguer–Decanteur De Laboratoire, Laboratory Mixer–Settlers."

Chemical Abstracts, vol. 83, No. 21, Abstract No. 176632, Nov. 24, 1975.

Chemical Abstracts, vol. 97, No. 23, Abstract No. 196829, Dec. 6, 1982.

PRODUCTION AND RECOVERY OF ORGANIC ACIDS

This is a continuation in part of the U.S. application titled "Production and Recovery of Organic Acids," filed on Oct. 10, 1996, application Ser. No. 08/728,836 now abandoned.

BACKGROUND OF THE INVENTION

The present invention relates to carboxylic acids such as lactic acid, and to processes for producing and recovering them.

Lactic acid has a number of commercial uses, for example in food manufacturing, pharmaceuticals, plastics, textiles, and as a starting material in various chemical processes. Lactic acid is commonly produced by fermentation of sugars, starch, or cheese whey, using microorganisms such as *Lactobacillus delbrueckii* to convert monosaccharides such as glucose, fructose, or galactose, or disaccharides such as sucrose or lactose, into lactic acid. The broth that results from fermentation contains unfermented sugars, carbohydrates, amino acids, proteins, and salts, as well as lactic acid. Some of these materials cause an undesirable color. The lactic acid therefore must be recovered from the fermentation broth before it can be put to any substantial use.

During the production of an organic acid such as lactic acid by fermentation, the increasing concentration of the acid in the fermentation broth reduces the pH. As the pH decreases, the growth of the microorganism is inhibited and eventually stops, and therefore acid production stops. To prevent this, the pH of the fermentation broth typically is controlled by adding a base for neutralization. Calcium bases, such as calcium hydroxide, have been preferred for neutralization of lactic acid fermentation broths, but their use results in the production of calcium lactate, which has some undesirable consequences for the ultimate recovery of the lactic acid. In particular, in order to recover free acid from the calcium lactate, a mineral acid such as sulfuric acid is often added. While this does permit recovery of free acid, it also generates gypsum as an unwanted byproduct. Further, the cost of the sulfuric acid is a significant factor in the overall cost of the process.

A need exists for improved processes that will permit production and recovery of organic acids at a desired level of purity and at a reduced cost.

SUMMARY OF THE INVENTION

The present invention relates to a process for producing a carboxylic acid, preferably one selected from the group consisting of mono-, di-, and tricarboxylic acids having 3–8 carbon atoms. Examples include lactic acid, citric acid, malic acid, maleic acid, fumaric acid, adipic acid, succinic acid, tartaric acid, α-ketoglutaric acid, and oxaloacetic acid.

The process includes production of the organic acid by fermentation employing a microorganism, resulting in an aqueous fermentation broth containing the organic acid. An alkaline earth base is added to the fermentation broth during and/or after the fermentation process, in an amount effective to allow growth of the microorganism producing the organic acid, thereby producing an alkaline earth salt of the organic acid in the broth. Biomass can optionally be removed from the broth. Whether the biomass is removed at this point in the process or not, an aqueous solution or dispersion is present that contains the alkaline earth salt of the organic acid. The alkaline earth salt of the organic acid, either with or without biomass, is then reacted with a source of ammonium ions selected from the group consisting of ammonia, ammonium salts, and substituted ammonium salts, thereby producing an ammonium salt or substituted ammonium salt of the organic acid. Free organic acid or a derivative thereof can then be separated and recovered.

The alkaline earth base is preferably a calcium base, for example selected from a group consisting of calcium hydroxide, calcium carbonate, calcium bicarbonate and calcium oxide, with calcium carbonate being especially preferred. The alkaline earth base can be added in an amount effective to control the pH of the broth between about 5.5 and about 7.0.

A preferred method for removal of the biomass from the broth is microfiltration. A preferred method for separating and recovering the free acid is salt-splitting electrodialysis. When salt-splitting electrodialysis is used, it is preferred to first reduce the level of soluble contaminants such as divalent cations in the solution by ion exchange.

When the organic acid produced is lactic acid, the equivalent ratio of ammonia to lactic acid is preferably between about 0.75 and about 2.0, most preferably between about 1.0 and 1.5. The pH after the exchange reaction with a source of ammonium ions is preferably between about 7.0 and about 11.0, most preferably between about 7.5 and 10.0. The optimum pH may vary with the source of the ammonium ions.

In one embodiment of the present invention, a process for producing lactic acid includes the steps of producing lactic acid by fermentation, resulting in an aqueous fermentation broth, adding a calcium base to the fermentation broth during and/or after the fermentation process to maintain the broth pH at a level high enough to allow growth of the microorganism producing the organic acid, thereby producing calcium lactate in the broth, removing biomass from the broth, thereby producing an aqueous solution or dispersion of calcium lactate, reacting the calcium lactate with a source of ammonium ions selected from the group consisting of ammonia, ammonium salts, and substituted ammonium salts, thereby producing ammonium lactate or a substituted ammonium lactate, removing contaminant cations by ion exchange, and separating and recovering free lactic acid by salt-splitting electrodialysis. Optionally the acid may be converted to a derivative, such as an ester, and recovered in that form.

The process can also include the step of heating the fermentation broth prior to removing biomass, to an extent effective to solubilize the majority of the calcium lactate present in the broth. The process can also include the step of concentrating the calcium lactate solution or dispersion prior to reaction with the source of ammonium ions, for example by crystallization of the calcium lactate followed by filtration.

The present invention presents opportunities for recycling streams generated at one point in the process for use at another point in the process. For example, in one embodiment of the present invention, a calcium carbonate precipitate is formed by the reaction of the calcium lactate with the source of ammonium ions, and the precipitate can be recycled to the fermentation broth. As another example, the salt-splitting electrodialysis step can generate ammonia, which can be recycled to the step in which calcium lactate is reacted with the source of ammonium ions.

An especially preferred embodiment of the present invention is a process for producing lactic acid that includes the steps of producing lactic acid by fermentation, resulting in an aqueous fermentation broth containing lactic acid, adding calcium carbonate to the fermentation broth, thereby producing calcium lactate in the broth, heating the broth to an extent effective to solubilize the majority of the calcium lactate, removing biomass from the broth by filtration, thereby producing an aqueous solution or dispersion of calcium lactate, concentrating calcium lactate by crystallization followed by filtration, adding a source of ammonium ions, selected from the group consisting of ammonium carbonate and a mixture of ammonia and carbon dioxide, to the aqueous solution or dispersion of calcium lactate, thereby producing ammonium lactate and calcium carbonate, separating the calcium carbonate and recycling it to the fermentation broth, removing contaminant cations by ion exchange, and separating and recovering free lactic acid by salt-splitting electrodialysis.

Another embodiment of the present invention concerns an improved process for producing lactic acid or a derivative thereof from a medium comprising calcium lactate salt, which salt is a product of fermentation, where (i) carbohydrates are fermented to lactic acid, (ii) a calcium base is used in the fermentation as neutralizing agent for pH adjustment so that an aqueous solution or dispersion of calcium lactate is formed, and (iii) a product calcium base is formed in the process. The improvement comprises (a) reacting a source of ammonium ions with the aqueous solution or dispersion of calcium lactate to form water soluble ammonium lactate and a product calcium base; (b) converting the water soluble ammonium lactate to lactic acid or a derivative thereof and a by-product that comprises ammonia; (c) separating the by-product that comprises ammonia; (d) using the by-product that comprises ammonia as a source of ammonium ions for step (a); (e) separating the product calcium base formed in step (a); and (f) using the product calcium base from step (e) as a neutralizing agent in the lactic acid fermentation.

In various specific embodiments of this improved process, conversion of the water soluble ammonium lactate to lactic acid or a derivative thereof in step (b) can be done by distillation. The separation of the by-product that comprises ammonia in step (c) can be done by, for example, distillation or crystallization.

The present invention has a number of advantages over prior art processes. It allows the production and recovery of organic acids at reduced cost. Further, it produces solutions of the organic acid having relatively high concentrations, thus reducing or eliminating the need for further concentration steps.

DESCRIPTION OF SPECIFIC EMBODIMENTS

Figure 1:
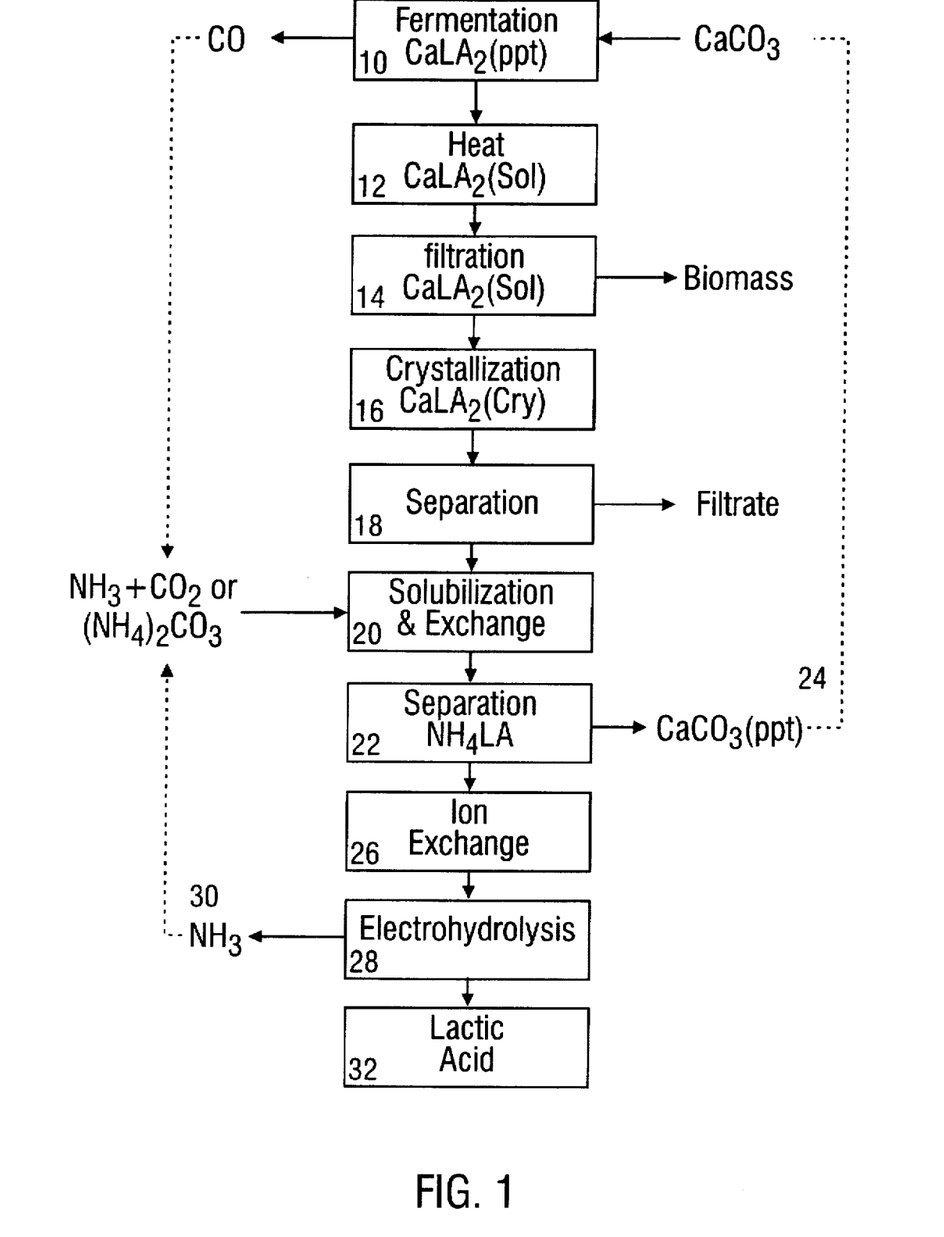
FIG. 1 is a process flow diagram for an organic acid production and recovery process in accordance with he present invention.

Referring to FIG. 1, a process in accordance with the present invention begins with the production of an organic acid by fermentation 10. Fermentation procedures and starting materials are well known to persons skilled in the art.

If the organic acid to be produced is lactic acid, a suitable fermentation procedure is as follows. The feed to this fermentation can consist of a mix of glucose syrup, light steepwater, corn gluten filtrate, and trace vitamins and minerals. Typical concentrations are about 110 gm. d.s./liter of glucose, 10 gm. d.s./liter of light steepwater, and 7 gm. d.s./liter of corn gluten filtrate. The trace vitamins and minerals can be (on a dry substance basis) 0.5 g/l of diammonium phosphate, 0.04 g/l of manganese sulfate, 68 ppm of choline, 4.4 ppm of riboflavin, and 2.0 ppm of niacin. Residual sulfur dioxide in the light steepwater and corn gluten filtrate can be neutralized with stoichiometric amounts of hydrogen peroxide. The organism can be of the species *L. casei* ssp. *rhamnosus*, for example ATCC 11443. The fermentation can be conducted at 108° F. The fermentation is finished when the glucose is exhausted, typically in about 20 hours. The yield on glucose will typically be about 95%. The fermentation broth will typically contain less than 25% by weight lactic acid. Often at least 80% by weight of the total lactate values in the broth are present as calcium lactate.

In order to maintain the rate of acid production, it is desirable to control the pH of the fermentation broth between about 5.5 and about 7.0. This is preferably done by adding to the broth an alkaline earth carbonate or bicarbonate base, preferably calcium carbonate. The addition of this calcium base is preferably done during the fermentation process. It keeps the pH of the broth from dropping too low, and results in the production of calcium lactate.

Figure 2:
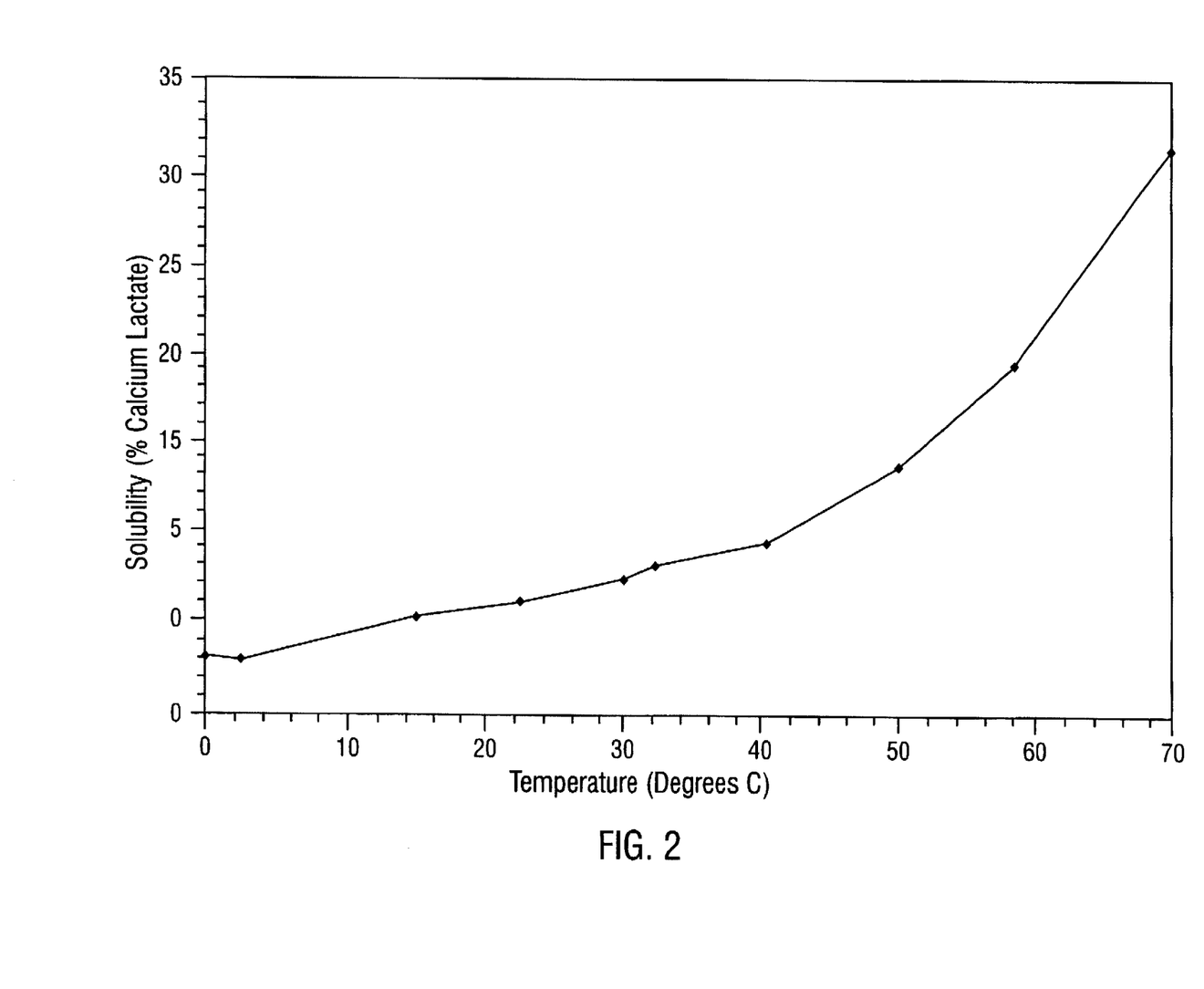
FIG. 2 is a graph of the solubility of calcium lactate in water at various temperatures.

The broth is heated 12 in order to solubilize the calcium lactate, preferably to a temperature of about 40°–60° C. FIG. 2 shows the solubility of calcium lactate at temperatures ranging from 0° C. to 70° C. Depending on the extent of the heating, some calcium lactate may remain in an undissolved state.

Next, biomass may be (but does not have to be) removed from the broth. If biomass is removed, it is preferably by tight membrane filtration 14. For example, the broth or liquor can be filtered using ultrafiltration or nanofiltration, for example with ceramic elements having a 0.02 micron pore size. Diafiltration can be used to attain a lactate recovery of at least 95%. The retentate stream, consisting of biomass and other insolubles, can be used as animal feed or in the alternative can be recycled to the fermentation bioreactor.

If the lactate broth is microfiltered, the permeate can then be nanofiltered at 140° F. on a nanofiltration membrane having a molecular weight cut-off of 250 to 1000. Diafiltration can be used to attain a recovery of calcium lactate of at least 95%.

As an alternative to filtration, other procedures such as centrifugation, filter pressing, or rotary vacuum filtration could be used to produce a substantially particulate-free liquor.

If biomass is not removed at this point in the process, then the processing of the broth and its contents can continue as described below with the biomass still present.

It is desirable to concentrate the solution of calcium lactate at this point, and this can be accomplished by crystallizing 16 the calcium lactate and then separating 18 the crystallized material, for example by filtration 18. Crystallization can be done using standard techniques known to those skilled in the art.

The next step in the process involves an exchange reaction 20. A source of ammonium ions, and preferably also a source of carbonate ions, are added to the solution. The source of ammonium ions can be in the form of ammonia, an ammonium salt, or a substituted ammonium salt or mixtures thereof. For example, the materials added in this step can be gaseous ammonia, aqueous ammonium hydroxide, ammonium carbonates or bicarbonates, gaseous mixtures of ammonia and carbon dioxide, or mixtures of one or more of these. If gaseous carbon dioxide is used, it can be taken from the gas stream liberated in the fermentation step 10.

A preferred process for the formation of the ammonium lactate (or other organic acid salt) is to first react the precipitated calcium lactate with ammonia in an aqueous medium to raise the pH of the reaction media to about 7.0 or higher, and then add ammonium carbonate or other source of ammonium ion to raise the pH to the desired level to form soluble ammonium lactate.

The result of this exchange reaction 20 is the formation of ammonium lactate and calcium carbonate. The calcium carbonate will typically precipitate, so it can be separated 22, for example by crystallization, and can optionally be recycled 24 to the fermentation step 10. The remaining solution can then be processed so as to recover the acid as such or as a derivative such as an ester. A preferred way of doing this is by salt-splitting electrodialysis.

Salt-splitting electrodialysis usually requires a relatively high purity solution as its starting material. Therefore, when salt-splitting electrodialysis 28 is used, the ammonium lactate solution is preferably first treated 26 with an ion exchange resin to reduce the residual level of divalent cations such as calcium to less than about 100 ppm, preferably less than about 5 ppm, more preferably less than about 2 ppm, to reduce fouling of the electrodialysis membranes. Exchangers such as Rohm and Haas Duolite C-467, weak acid cation resin, or the like may be used for this purpose. This procedure extends the life of the electrohydrolysis membranes.

The remaining solution can be separated into free lactic acid and ammonia, for example by salt-splitting electrodialysis 28. Salt splitting electrodialysis (SS-ED) is capable of splitting a salt into its corresponding acid and base. It uses electrical current to drive salt ions through cationic and anionic permeable membranes, and also uses a special bipolar membrane (one side anionic and one side cationic) to split water into $H^+$ and $OH^-$ to combine with the salt anion and cation respectively. Only charged compounds are transferred to the product streams.

Electrodialysis has the advantage of being able to produce an acid (or base) from a salt solution without forming another salt as a byproduct. Further, salt splitting electrodialysis produces a high quality end product. The major drawbacks of salt splitting electrodialysis are the yield loss, electrical consumption, and the cost and life of the membranes. The yield or lactic acid recovery can be improved at additional electrical and capital costs. Electrodialysis apparatus and conditions are disclosed in U.S. Pat. Nos. 5,198,086, 5,250,159, and 5,268,079, each of which is incorporated here by reference.

The ammonia generated by electrohydrolysis can be recycled 30 to the exchange reaction 20. This then leaves free lactic acid 32, which can optionally be further purified, for example by carbon treatment or ion exchange. The free acid optionally may be derivatized, for example to lactic acid esters, or polymerized to form polylactic acid. The product may also be subjected to further purification steps, such as carbon treatment, molecular distillation, or liquid/liquid extraction.

EXAMPLE 1

A series of reactions was performed in 120 ml, screw cap bottles containing the quantities of components listed in Table 1.

TABLE 1

Experimental Design and Data

| Bottle Number | Calcium Lactate Grams | Saturated $(NH_4)_2CO_3$ Grams | Water Grams | Total Wt. Grams | Ammonia/Lactic Molar Ratio |
|---|---|---|---|---|---|
| 1 | 5.0005 | 18.05 | 17.10 | 40.1505 | 2.01 |
| 2 | 5.0079 | 13.51 | 21.63 | 40.1479 | 1.50 |
| 3 | 5.0024 | 9.03 | 26.02 | 40.0524 | 1.01 |
| 4 | 5.0013 | 6.79 | 28.26 | 40.0513 | 0.76 |
| 5 | 5.0043 | 4.50 | 30.52 | 40.0243 | 0.50 |
| 6 | 5.0008 | 2.28 | 32.81 | 40.0908 | 0.25 |
| 7 | 5.0004 | 0.00 | 35.01 | 40.0104 | 0.00 |

Solid calcium lactate (Sigma Chem. Co., Lot 113H2522, 60.23% lactate, 13.92% calcium, 25.85% water) was added to each bottle followed by the appropriate quantity of water and the aqueous, saturated ammonium carbonate solution. The saturated ammonium carbonate solution was prepared by stirring excess ammonium carbonate (Sigma Chem. Co., Lot 26H3613, 32.3% $NH_3$) with water for 24 hours in a sealed flask at 24° C. and separating the solution by filtration. The pH of this saturated solution was 8.41 and contained 6.46% $NH_3$. The bottles were sealed and vigorously shaken at 24° C. for 4 hours. The solids were allowed to settle for 20 minutes and the supernatant was clarified through 0.45 micron filters. The pH of the filtered solutions was measured and analyzed for lactic acid, calcium and carbonate. The results of these analyses are shown in Table 2.

TABLE 2

Analytical Data

| Bottle Number | Total Water Grams | % of Total Lactic Acid Soluble | % of Total Calcium Soluble | % of Total $CO_3$ Soluble |
|---|---|---|---|---|
| 1 | 33.15 | 89.56 | 0.21 | 59.76 |
| 2 | 33.97 | 93.75 | 0.30 | 45.11 |
| 3 | 34.70 | 94.57 | 8.26 | 19.26 |
| 4 | 35.11 | 93.25 | 20.45 | 19.55 |
| 5 | 35.49 | 79.29 | 25.89 | 19.42 |
| 6 | 35.97 | 70.12 | 37.46 | 12.48 |
| 7 | 36.30 | 62.75 | 43.15 | 0.00 |

Figure 3:
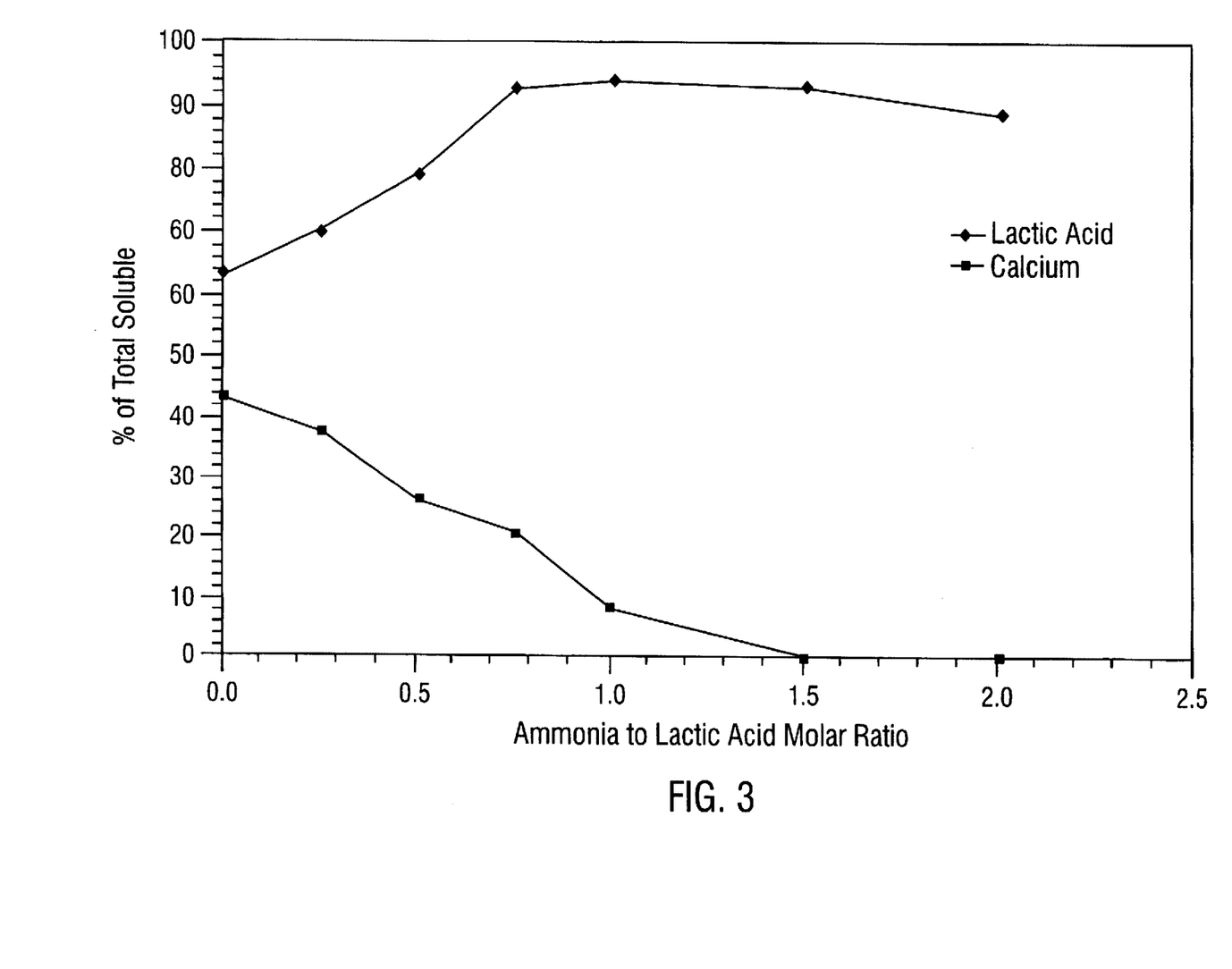
FIGS. 3, 4, and 5 are graphs reflecting test results that are described in Example 1.
Figure 4:
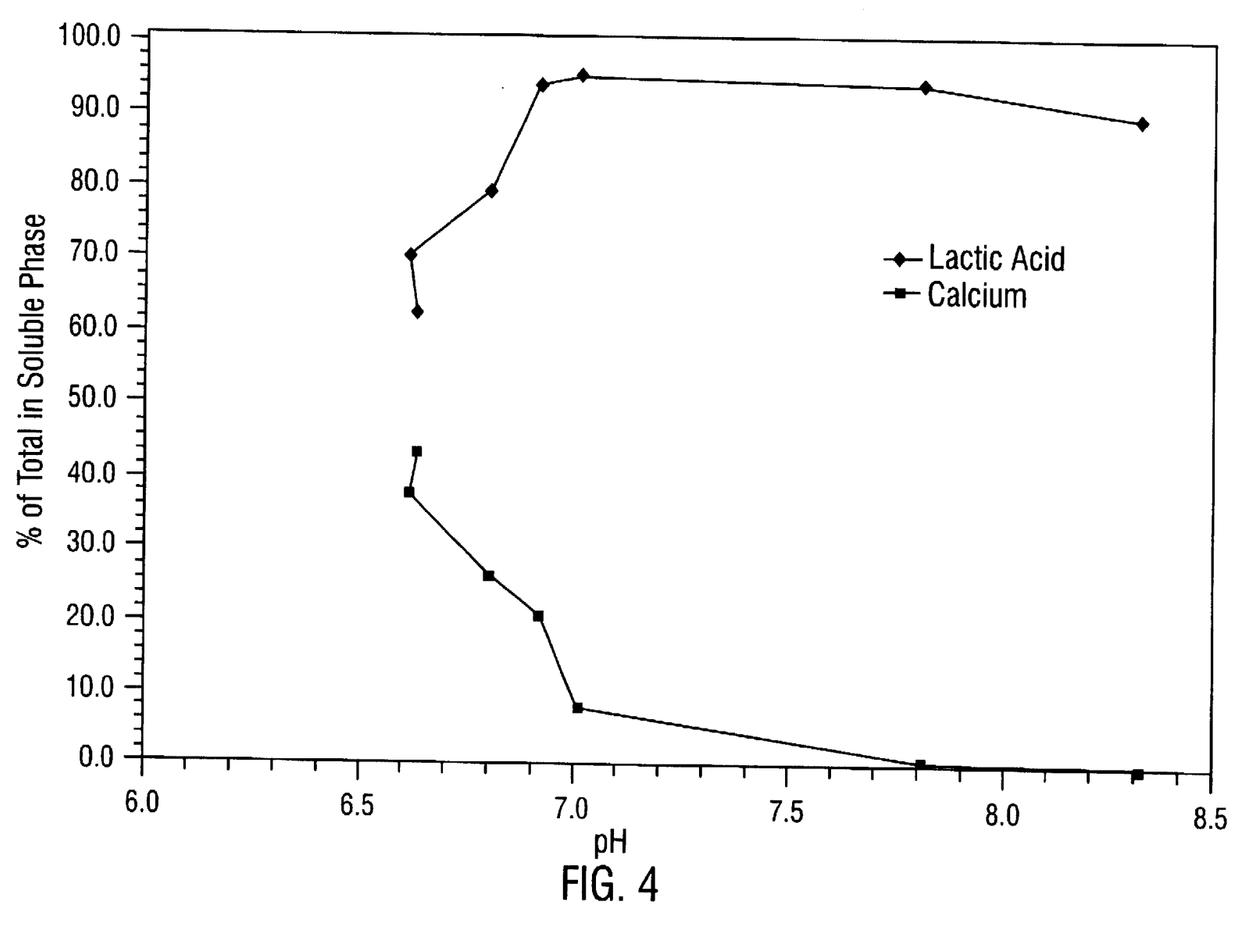
Figure 5:
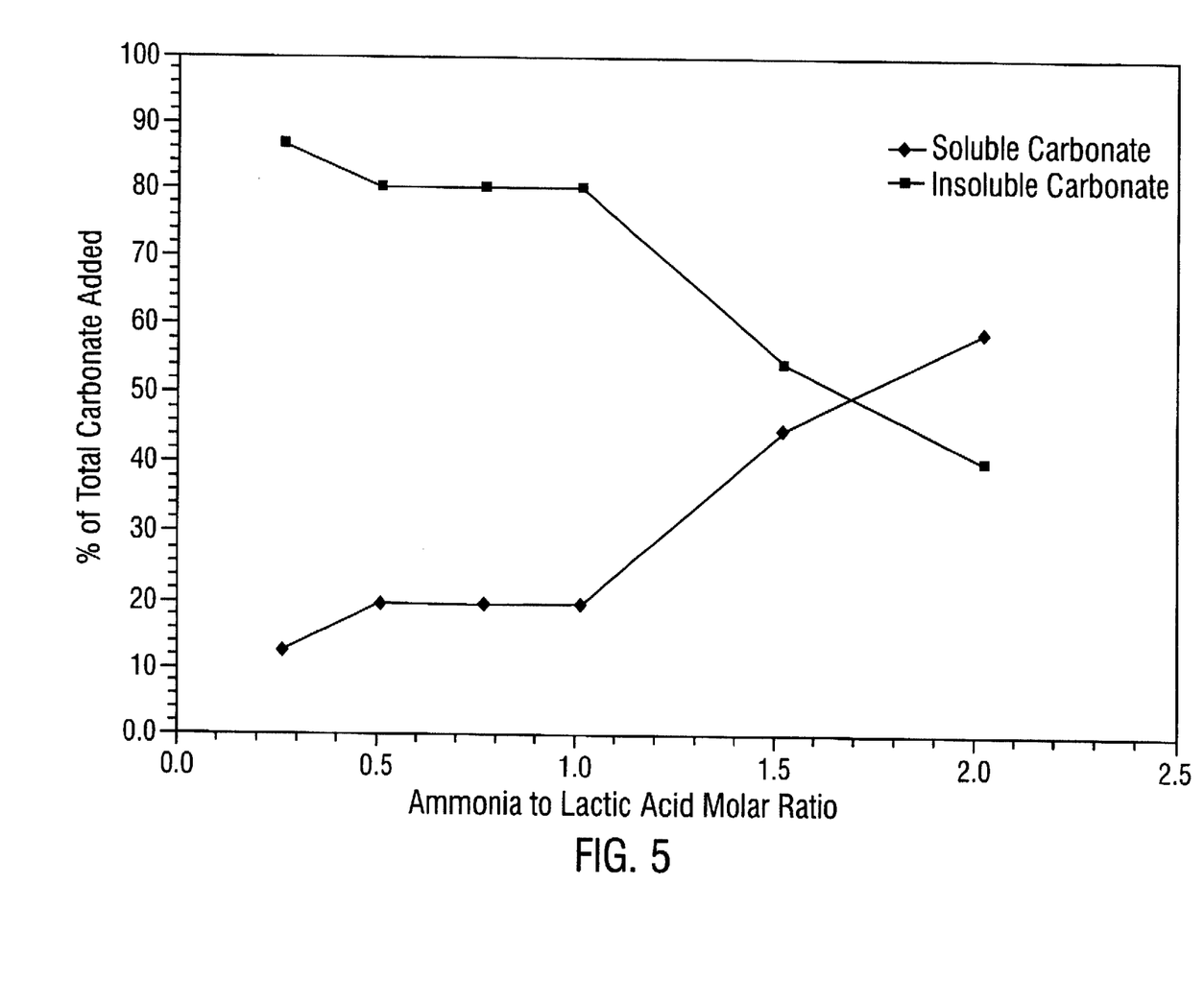

Lactic acid and carbonate were determined by High Pressure Liquid Chromatography with a Dionex ion exclusion column (IonPac ICE-AS6) with an eluent flow rate of 1 ml/min with 0.4 mM heptafluorobutyric acid. The detector was a conductivity detector with chemical suppression. The column was regenerated with 0.01M tetrabutylammonium hydroxide at 5 ml/min. Calcium was determined by atomic spectroscopy. The percent of total lactic acid, calcium and $CO_3$ which is soluble was calculated on the basis of the total grams of water in the system. This is a combination of the water contained in the calcium lactate, saturated ammonium carbonate and added water. The calculated results are shown in Table 3 and are represented in FIGS. 3, 4, and 5.

TABLE 3

Calculated Data

| Bottle Number | pH Final | % Lactic Acid In Solution | ppm Calcium In Solution | % Carbonate In Solution |
|---|---|---|---|---|
| 1 | 8.33 | 7.57 | 43 | 3.70 |
| 2 | 7.82 | 7.76 | 59 | 2.04 |
| 3 | 7.01 | 7.67 | 1590 | 0.57 |
| 4 | 6.92 | 7.48 | 3893 | 0.43 |
| 5 | 6.80 | 6.30 | 4877 | 0.28 |
| 6 | 6.62 | 5.50 | 6961 | 0.09 |
| 7 | 6.63 | 4.88 | 7945 | 0.00 |

At an ammonia to lactic acid mole ratio of one, greater than 94% of the lactic acid was solubilized as the ammonium lactate while greater than 90% of the calcium was insoluble. As this ratio increased toward two, the insoluble calcium increased to greater than 99%.

EXAMPLE 2

Calcium lactate (10.03 g), water (43.12 g) and saturated ammonium carbonate (26.92 g) were placed in a 250 ml screw cap bottle and shaken vigorously for two hours and allowed to stand overnight at 24° C. This is approximately double the quantities of reagents used in Example 1, Bottle 2 where the molar ratio of ammonia to lactic acid is 1.5/1. The mixture was separated using a medium, porous glass filter and the solid fraction was washed three times with about 20 ml of ice cold water. The total weight of the filtrates was 134.38 g and contained 42.5 ppm calcium and 4.60% lactic acid. The recovery of the lactic acid in the soluble phase was 102%. The weight of the precipitate was 4.4140 g and contained 31.0% calcium, a recovery of 98%. A portion of the precipitate (0.5201 g) was extracted with 2.0866 g of hot water and the mixture filtered through a 0.45 micron filter disc. This filtrate contained only 6 ppm of lactic acid. The Infra-red analysis spectrum of the precipitate was consistent with that of carbonate with some slight contaminant of organic matter. This data is consistent with a calcium carbonate precipitate which contains only traces of lactic acid.

The preceding description of specific embodiments of the present invention is not intended to be a complete list of every possible embodiment of the invention. Persons skilled in this field will recognize that modifications can be made to the specific embodiments described here that would be within the scope of the present invention.

We claim:

1. A process for producing an organic acid, comprising the steps of:

producing by fermentation an organic acid selected from the group consisting of mono-, di-, and tricarboxylic acids having 3–8 carbon atoms, resulting in an aqueous fermentation broth;

adding an alkaline earth base to the fermentation broth in amount effective to maintain the broth pH at a level high enough to allow continued production of the organic acid, thereby producing an alkaline earth salt of the organic acid in the broth;

reacting the alkaline earth salt of the organic acid with a source of ammonium ions selected from the group consisting of ammonia, ammonium salts, substituted ammonium salts, and mixtures thereof, thereby producing an aqueous solution or dispersion containing ammonium salt or substituted ammonium salt of the organic acid and divalent cations;

reducing the concentration of divalent cations to a level sufficient to permit salt-splitting electrodialysis;

converting the ammonium or substituted ammonium salt of the organic acid to free organic acid or a derivative thereof; and recovering the free organic acid or derivative thereof.

2. The process of claim 1, where the organic acid is lactic acid.

3. The process of claim 1, where the alkaline earth base is a calcium base.

4. The process of claim 1, where the alkaline earth base is selected from the group consisting of calcium carbonate, calcium bicarbonate, calcium oxide, and calcium hydroxide.

5. The process of claim 1, where the alkaline earth base is added during the fermentation process.

6. The process of claim 1, where the alkaline earth base is added in an amount effective to control the pH of the broth between about 5.5 and about 7.0.

7. The process of claim 1, where biomass is removed from the broth prior to reacting the alkaline earth salt of the organic acid with the source of ammonium ions.

8. The process of claim 7, where biomass is removed from the broth by microfiltration.

9. The process of claim 1, where the source of ammonium ions comprises ammonia.

10. The process of claim 1, where the source of ammonium ions comprises a mixture of ammonia and at least one ammonium salt or substituted ammonium salt.

11. The process of claim 1, where the source of ammonium ions comprises ammonium carbonate.

12. The process of claim 1, where the alkaline earth salt of the organic acid is reacted with ammonia in an aqueous medium to raise the pH to above about 7, and then ammonium carbonate is added thereto.

13. The process of claim 1, where the derivative of the organic acid is an ester.

14. The process of claim 1, where the ammonium or substituted ammonium salt of the organic acid is converted to the free acid or derivative thereof by salt-splitting electrodialysis.

15. The process of claim 14, where the concentration of divalent cations is reduced prior to salt-splitting electrodialysis by ion exchange.

16. The process of claim 1, where the pH after the reaction with a source of ammonium ions is between about 7.0 and about 11.0.

17. The process of claim 1, where the pH after the reaction with a source of ammonium ions is between about 7.5 and about 10.0.

18. A process for producing lactic acid, comprising the steps of:

producing lactic acid by fermentation, resulting in an aqueous fermentation broth;

adding a calcium base to the fermentation broth in an amount effective to maintain the broth pH at a level high enough to allow continued production of the lactic acid, thereby producing calcium lactate in the broth;

reacting the calcium lactate with a source of ammonium ions selected from the group consisting of ammonia, ammonium salts, substituted ammonium salts, and mixtures thereof, thereby producing aqueous solution or dispersion containing an ammonium lactate or substituted ammonium lactate divalent cations;

reducing the concentration of divalent cations to a level sufficient to permit salt-splitting electrodialysis;

converting the ammonium or substituted ammonium lactate to free lactic acid or a derivative thereof; and recovering the free lactic acid or derivative thereof.

19. The process of claim 18, where the calcium base is calcium carbonate.

20. The process of claim 18, where the calcium base is added in an amount effective to control the pH of the broth between about 5.5 and about 7.0.

21. The process of claim 18, where biomass is removed from the broth prior to reacting the calcium lactate with the source of ammonium ions.

22. The process of claim 21, where the biomass is removed from the broth by microfiltration.

23. The process of claim 18, where the source of ammonium ions comprises ammonia.

24. The process of claim 18, where the source of ammonium ions comprises a mixture of ammonia and at least one ammonium salt or substituted ammonium salt.

25. The process of claim 18, where the source of ammonium ions comprises ammonium carbonate.

26. The process of claim 18, further comprising the step of heating the fermentation broth prior to removing biomass, to an extent effective to solubilize the majority of the calcium lactate present in the broth.

27. The process of claim 18, where the calcium lactate is reacted with ammonia in an aqueous medium to raise the pH to above about 7, and then ammonium carbonate is added thereto.

28. The process of claim 18, further comprising the step of concentrating the calcium lactate solution or dispersion prior to reaction with the source of ammonium ions by crystallization of the calcium lactate followed by filtration.

29. The process of claim 18, where a calcium carbonate precipitate is formed by the reaction of the calcium lactate with the source of ammonium ions, and the precipitate is recycled to the fermentation broth.

30. The process of claim 18, where the ammonium salt or substituted ammonium salt of lactic acid is converted to free lactic acid or derivative thereof by salt splitting electrodialysis.

31. The process of claim 30, where the concentration of divalent cations is reduced prior to salt splitting electrodialysis by ion exchange.

32. The process of claim 18, where the equivalent ratio of ammonia to lactic acid is between about 0.75 and 2.0.

33. The process of claim 18, where the equivalent ratio of ammonia to lactic acid is between about 1.0 and 1.5.

34. The process of claim 18, where the pH after the reaction with a source of ammonium ions is between about 7.0 and about 11.0.

35. The process of claim 18, where the pH after the reaction with a source of ammonium ions is between about 7.5 and about 10.0.

36. The process of claim 18, where the salt-splitting electrodialysis generates ammonia, which is recycled to the reaction of calcium lactate with the source of ammonium ions.

37. A process for producing lactic acid, comprising the steps of:
producing lactic acid by fermentation, resulting in an aqueous fermentation broth;
adding calcium carbonate to the fermentation broth, thereby producing calcium lactate in the broth;
solubilizing the majority of the calcium lactate;
removing biomass from the broth by filtration, thereby producing an aqueous solution or dispersion of calcium lactate;
adding a source of ammonium ions, selected from the group consisting of ammonium carbonate and a mixture of ammonia and carbon dioxide, to the aqueous solution or dispersion of calcium lactate, thereby producing ammonium lactate and calcium carbonate;
separating the calcium carbonate and recycling it to the fermentation broth;
removing contaminant cations by ion exchange; and
converting the ammonium lactate to free lactic acid by salt-splitting electrodialysis.

38. In a process for producing lactic acid or a derivative thereof from a medium comprising calcium lactate salt, which salt is a product of fermentation, where (i) carbohydrates are fermented to lactic acid, (ii) a calcium base is used in the fermentation as neutralizing agent for pH adjustment so that an aqueous solution or dispersion of calcium lactate is formed, and (iii) a product calcium base is formed in the process, the improvement comprising:

(a) reacting a source of ammonium ions with the aqueous solution or dispersion of calcium lactate to form water soluble ammonium lactate and a product calcium base;

(b) converting the water soluble ammonium lactate to lactic acid or a derivative thereof and a by-product that comprises ammonia;

(c) separating the by-product that comprises ammonia;

(d) using the by-product that comprises ammonia as a source of ammonium ions for step (a);

(e) separating the product calcium base formed in step (a); and (f) using the product calcium base from step (e) as a neutralizing agent in the lactic acid fermentation.

39. The process of claim 38, where the conversion of the water soluble ammonium lactate to lactic acid or a derivative thereof in step (b) is done by electrodialysis.

40. The process of claim 39, where prior to the salt-splitting electrodialysis, contaminant cations are removed by ion exchange.

41. The process of claim 38, where the conversion of the water soluble ammonium lactate to lactic acid or a derivative thereof in step (b) is done using bipolar membranes.

42. The process of claim 38, where the conversion of the water soluble ammonium lactate to lactic acid or a derivative thereof in step (b) is done by distillation.

43. The process of claim 38, where the source of ammonium ions is selected from the group consisting of gaseous ammonia, aqueous ammonium hydroxide, ammonium carbonates, or bicarbonates, mixtures of ammonia with carbon dioxide, and combinations thereof.

44. The process of claim 38, where the pH in step (a) after the reaction with the source of ammonium ions is between about 7.0 and about 11.0.

45. The process of claim 38, where the pH in step (a) after the reaction with the source of ammonium ions is between about 7.5 and about 10.0.

46. The process of claim 38, where the separation of the by-product that comprises ammonia in step (c) is done by distillation.

47. The process of claim 38, where the separation of the by-product that comprises ammonia in step (c) is done by crystallization.

48. The process of claim 38, where the ammonium lactate is concentrated prior to the conversion in step (b).

49. The process of claim 38, where the product calcium base is selected from a group consisting of calcium hydroxide, calcium carbonate, calcium bicarbonate, and calcium carbonate.

50. The process of claim 38, where prior to the conversion in step (b), an ion exchange is performed to reduce the concentration of divalent cations in solution to less than about 100 ppm, and the conversion of step (b) is then done by salt-splitting electrodialysis.

51. The process of claim 1, where the concentration of divalent cations is reduced prior to the conversion step to less than about 100 ppm.

52. The process of claim 1, where the concentration of divalent cations is reduced prior to the conversion step to less than about 5 ppm.

53. The process of claim 1, where the concentration of divalent cations is reduced prior to the conversion step to less than about 2 ppm.

54. The process of claim 18, where the concentration of divalent cations is reduced prior to the conversion step to less than about 100 ppm.

55. The process of claim 18, where the concentration of divalent cations is reduced prior to the conversion step to less than about 5 ppm.

56. The process of claim 18, where the concentration of divalent cations is reduced prior to the conversion step to less than about 2 ppm.

57. The process of claim 1, where the conversion to the free acid or derivative thereof is done by distillation.

58. The process of claim 18, where the conversion to the free acid or derivative thereof is done by distillation.

* * * * *

UNITED STATES PATENT AND TRADEMARK OFFICE
CERTIFICATE OF CORRECTION

PATENT NO.    : 5,766,439

DATED         : June 16, 1998

INVENTOR(S)   : Aharon M. Eyal et al.

It is certified that error appears in the above-identified patent and that said Letters Patent is hereby corrected as shown below:

Claim 1, column 7, line 59, before "amount" insert --an--.

Claim 49, column 11, lines 5-6, change "calcium carbonate, calcium bicarbonate, and calcium carbonate" to --calcium carbonate, and calcium bicarbonate--.

Signed and Sealed this

Twelfth Day of January, 1999

Attest:

*Attesting Officer*

*Acting Commissioner of Patents and Trademarks*